(12) United States Patent
Aslam et al.

(10) Patent No.: US 7,615,189 B2
(45) Date of Patent: Nov. 10, 2009

(54) ANALYTE ACCUMULATION DEVICE

(75) Inventors: Dean M. Aslam, Okemos, MI (US);
Edward T. Zellers, Ann Arbor, MI (US);
Yang Lu, Lansing, MI (US)

(73) Assignees: Board of Trustees of Michigan State University, East Lansing, MI (US);
Regents of the University of Michigan, Ann Arbor, MI (US)

( * ) Notice: Subject to any disclaimer, the term of this patent is extended or adjusted under 35 U.S.C. 154(b) by 594 days.

(21) Appl. No.: 11/145,292

(22) Filed: Jun. 3, 2005

(65) Prior Publication Data

US 2006/0120919 A1 Jun. 8, 2006

Related U.S. Application Data

(60) Provisional application No. 60/576,954, filed on Jun. 4, 2004.

(51) Int. Cl.
*G01N 33/00* (2006.01)
(52) U.S. Cl. .............................. 422/57; 422/50; 422/55; 422/68.1; 422/99
(58) Field of Classification Search .................. 422/50, 422/55, 57, 68.1, 99
See application file for complete search history.

(56) References Cited

U.S. PATENT DOCUMENTS 6,685,810 B2 * 2/2004 Noca et al. .................. 204/450

* cited by examiner

*Primary Examiner*—Sam P Siefke
(74) *Attorney, Agent, or Firm*—Ian C. McLeod

(57) ABSTRACT

A device for accumulation of vapor analytes incorporating nanotubes grown by CVD is described. The devices are used in sensors and as a preconcentrator for a gas chromatograph.

6 Claims, 19 Drawing Sheets

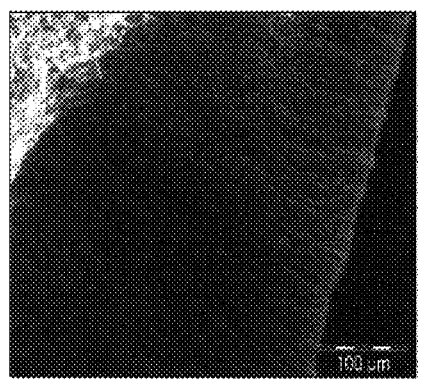
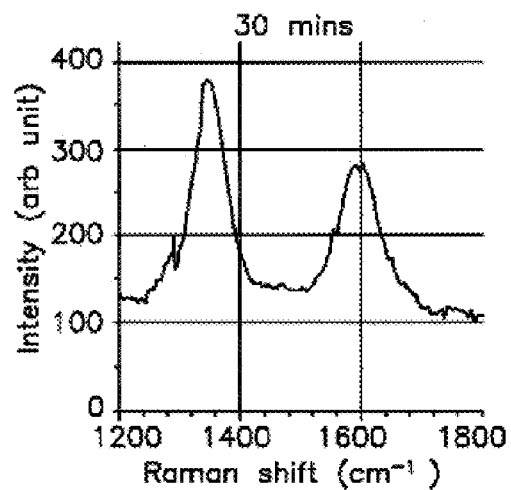
FIG. 3A  FIG. 3B
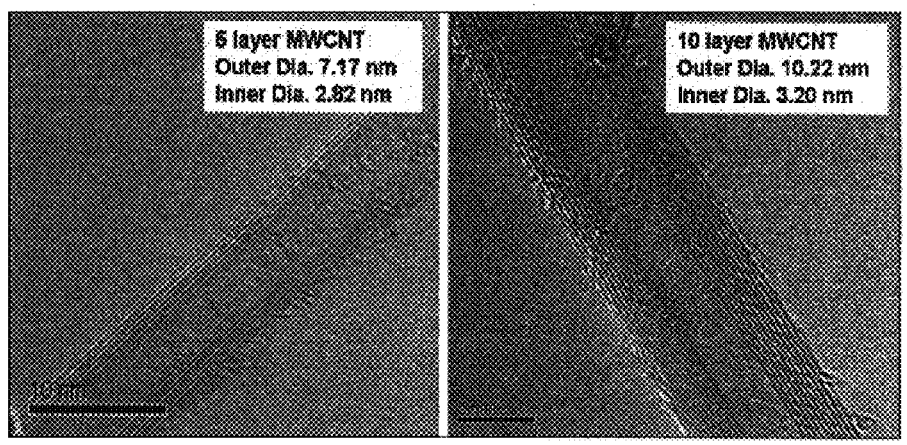
FIG. 4A  FIG. 4B

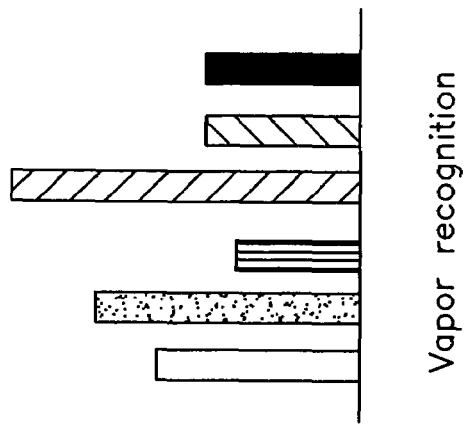
FIG. 13B
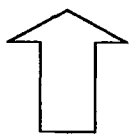
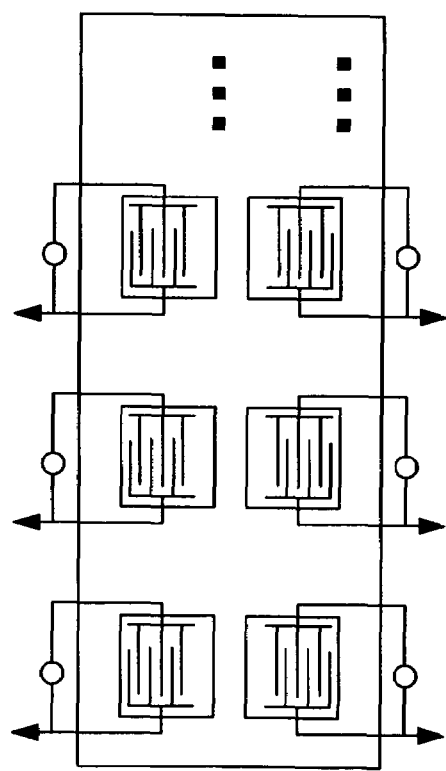
FIG. 13A

ANALYTE ACCUMULATION DEVICE

CROSS-REFERENCE TO RELATED APPLICATIONS

This application relies for priority on Provisional Application Ser. No. 60/576,954, filed Jun. 4, 2004.

STATEMENT REGARDING FEDERALLY SPONSORED RESEARCH OR DEVELOPMENT

This invention was made by or under contract with the National Science Foundation of the United States Government under Contract No.: EEC-9986866. The government has certain rights in this invention.

BACKGROUND OF THE INVENTION (1) Field of the Invention

This invention generally relates to gas accumulation for sensors or detectors such as a micro-scale gas chromatograph and method of use. In particular the present invention relates to a device which uses carbon nanotubes to accumulate an analyte.

(2) Description of the Related Art

The related art in the use of carbon nanotubes in sensors (detectors) is described for instance in US 2005/0045477 A1 to Wei et al, US 2005/0095722 A1 to McGill et al and US 2005/0090015 A1 to Hartmann-Thompson. Generally the nanotubes are formed, harvested and then used to coat a plate or substrate. These steps are time consuming and prone to error and chemical contamination. There is a need for improvement.

OBJECTS

It is therefore an object of the present invention to provide improved devices and method for detection of analytes. These and other objects will become increasingly apparent by reference to the following description and the drawings.

SUMMARY OF THE INVENTION

The present invention relates to an analyte accumulation device which comprises:

(a) a non-conductive substrate in a container means having an opening for inlet of the analyte;

(b) a conductive strip bound to the plate;

(c) a strip of a metal catalyst, which allows growth of nanotubes, mounted on the conductive strip; and (d) a lawn of carbon nanotubes which have been grown by chemical vapor deposition on the strip of the metal catalyst, wherein the nanotubes are adapted to accumulate a gaseous or liquid analyte inside the container means. Preferably the device is a MEMS device and strips have a surface area in the range of 50 millimeter$^2$ or less. Preferably the strip of the catalyst is a transition metal, the conductive strip is a metal, a conductor or semiconductor and the substrate is a semiconductor or insulator. Preferably the substrate is a plate with a series of channels with the carbon nanotubes in the channels. Preferably the substrate is a plate with a series of parallel channels supporting the nanotubes. Preferably an outlet of the device is integrated with a detector means for detecting the analyte. Preferably the device is adapted as a preconcentrator for a gas chromatograph. Preferably the device is integrated with a sensor means.

The present invention also relates to a method for the accumulation of an analyte for detection which comprises:

(a) providing a device which comprises (a) a non-conductive substrate in a container means having an opening for inlet of the analyte; a conductive strip bound to the plate; a strip of a metal catalyst, which allows growth of nanotubes, mounted on the conductive strip; and (d) a lawn of carbon nanotubes which have been grown by chemical vapor deposition on the strip of the metal catalyst, wherein the nanotubes are adapted to accumulate a gaseous or liquid analyte inside the container means;

(b) introducing the analyte into the container through the inlet means so as to accumulate the analyte in the carbon nanotubes; and (d) detecting the analyte. Preferably the detecting is with a detection means. Preferably the detecting is with a gas chromatograph. Preferably the detecting is with a gas sensor means. Preferably the strip of the catalyst is a transition metal, the conductive strip is a metal, a conductor or semiconductor and the substrate is a semiconductor or insulator. Preferably the substrate is a plate with a series of channels with the carbon nanotubes in the channels. Preferably the device is a MEMS device, wherein a surface area of the conductive strip is in the range of about 50 millimeters$^2$ or less.

The present invention also relates to a device as a sensor wherein the carbon nanotubes are in physical contact so as to provide a resistor and wherein resistance of the nanotubes changes when the nanotubes contain the chemical to enable detection of the chemical as the analyte. Preferably the carbon nanotubes have multiple monolayers of the carbon. Preferably the nanotubes have a single monolayer of the carbon.

The use of carbon nanotubes (CNTs) as components in a microanalytical system for vapor analysis is described. These CNTs can be grown in situ using known chemical vapor deposition methods on the surfaces of microfabricated channels or other structures and therein serve as media for preconcentration, separation, and detection of a wide range of vapors in a microanalytical system. The structure, the thickness, and density of the CNTs can be varied to suit the particular function of the microsystem sub-system component. For the preconcentration sub-system, varying the thickness, surface area and pore structure can affect capacity and thermal desorption efficiency. For the separation sub-system, similar changes in the physical properties of the CNT layer can affect retention and separation of mixture components. For the detection sub-system, deposition of CNT layers of different structures on a series of mass sensitive or electronic-conduction sensitive sensor can affect vapor detection sensitivity and selectivity. The ability to deposit CNT layers in situ and to vary the layer properties are enabling features. The application of this type of material and this process to the development of microanalytical systems (i.e., miniaturized chemical analysis systems made using Si-microfabrication technology) development is unique.

The use of a single- or multi-walled carbon nanotubes (CNTs), consisting of cylindrical structures made of carbon having diameters on the order of a few nanometers and lengths ranging up to tens or hundreds of micrometers, as vapor-sorptive media in a microfabricated analytical system intended for vapor analysis is described. The invention relies on the deposition, or in situ growth, of such CNTs from gas-phase precursors on the surfaces of substrates/structures of various shapes and functions within the microanalytical system using known chemical vapor deposition methods. Such surface CNT layers can serve as adsorbent media for vapor preconcentration and subsequent thermal desorption, for chromatographic vapor separations, and for vapor detection of a wide range of vapors depending on the structure upon which the CNTs are deposited. The physical form, size thickness, density, specific surface area, pore size distribution of the CNTs can be varied potentially to suit the particular function of the microsystem sub-system component.

For the preconcentration sub-system, varying the thickness, surface area and pore structure can affect capacity and thermal desorption efficiency. The ability to grow CNTs directly onto the surface of underlying heater structures enhances thermal contact and thereby thermal desorption efficiency. For the separation sub-system, similar changes in the physical properties of the CNT layer affect retention and separation of mixture components. For the detection sub-system, deposition of CNT layers of different structures on one or a series (array) of mass sensitive or electronic-conduction sensitive sensors (or other sensors that respond to changes in a surface layer of CNTs) can affect different vapor detection sensitivity and selectivity. The ability to deposit CNT layers in situ and to vary the layer properties are enabling features.

Key unique aspects of this invention include the following. First, the ability to grow these CNTs, in situ, and to pattern where they grow, how thick a layer is formed, and what the specific surface area is, are important. In particular, the ability to grow conformal layers of CNTs onto the walls of etched, high-aspect-ratio silicon structures and to use such coated structures for vapor preconcentration is a primary focus of this disclosure. Similar coating onto etched-Si channels for vapor-mixture separations, and coating onto the surfaces of chemical sensors for vapor detection are also potential applications. These are novel applications of these materials, which address a need for such a porous material in developing microanalytical systems for vapor analysis. The potential ability to modify the physical and chemical and electronic properties of the CNTs in ways that facilitate their use in this application is also a key feature. For example, processing modifications can yield adjustments in the length, surface area, pore size, areal and bulk density, and wall structure (multi-wall or single wall). The modification of CNT properties by processing variations is known, but the use of this capability to alter the CNTs in ways that are relevant to the proposed applications is new.

An important application for the CNTs is as the adsorbent in a thermally desorbed vapor preconcentrator in gas chromatography. The CNTs are deposited directly onto the surface of a microfabricated heater structure that comprises the body of the preconcentrator (after sealing and installing inlet and outlet ports for introduction of vapor samples and subsequent desorption to downstream components, such as a separation channel and/or sensor array) of the microanalytical system.

BRIEF DESCRIPTION OF THE DRAWINGS

FIG. 3 is a SEM image of scraped MWCNT film grown for 30 minutes at 650° C.

FIG. 4A is a SEM image of 5 layer MWCNT with an outer diameter of 7.17 nm and an inner diameter of 2.82 nm.

FIG. 4B is a SEM image of a 10 layer MWCNT with an outer diameter of 10.22 nm and an inner diameter of 3.20 nm.

FIG. 5A shows dry-etched Si channels. FIG. 5B shows channels after lithography. FIG. 5C shows channels after MWCNT synthesis, and FIG. 5D shows close up of MWCNTs in the channels.

FIG. 8A is a basic structure; FIGS. 8C to 8F are structures showing single-stage etched-silicon heater structures.

FIG. 12A is a conceptual diagram of stacked, interconnected series of channel chips; FIG. 12B is a scanning electron micrograph of a spiral-etched column chip. Insert FIG. 12C shows the dimensions of the channel cross section. FIGS. 12D and 12E are photographs of individual channel chips with spiral and serpentine etch and total length of just less than 1 meter.

FIG. 13A is a conceptual drawing of an array of sensors, each coated with a different CNT, leading to a characteristic response pattern for a hypothetical vapor that can be used for vapor recognition as in FIG. 13B ('finger printing').

FIG. 15A shows dry-etched Si channels, FIG. 15B shows channels after lithography, FIG. 15C shows channels after MWCNT synthesis and FIG. 15D shows closeup of MWCNTs in the channels.

DESCRIPTION OF PREFERRED EMBODIMENTS

Figure 1:
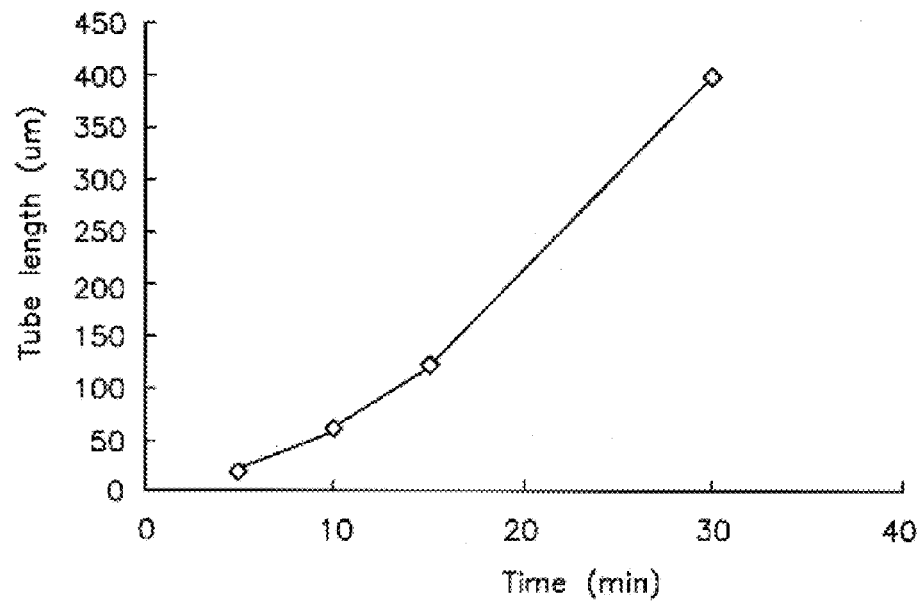
FIG. 1 is a graph of MWCNT length as a function of synthesis time.

The nanostructures present in Multiwall carbon nanotubes (MWCNT) provide a very large surface area as compared to conventional materials. As the number of layers in a MWCNT, and therefore diameter of the MWCNT, can be changed through growth conditions, the storage or adsorption sites for different gas molecules can be adjusted in a unique way. Experimental results show that the desorption temperature of MWCNT is approximately 200° C. as compared to 300° C. for a typical adsorption material, which dramatically reduces the energy consumption in the preconcentrator focuser (PCF) stage of a micro gas chromatograph (μGC) making MWCNT an ideal material for an on-chip μGC.

Initially, MWCNT were produced by using liquid catalyst which was made by dissolving log ferric nitride in 100 ml methanol. The silicon sample was soaked by the catalyst solution then dried in 80° C. Before growing MWCNT, the sample was treated by hydrogen plasma for 10 minutes at 30 torr, and then the reaction gas which contains 33% methane and 67% of hydrogen was introduced at flow rate of 30 sccm. The microwave power was controlled at 1600 W and the synthesis time is 15 minutes. The MWCNT sample showed high desorption efficiency at low desorption temperature and the results were reproducible. But it is very difficult to control the liquid catalyst to do selective seeding and keep the outside of the PCF channel clean. Accordingly, (i) the reproducibility of high-quality MWCNTs selectively grown in PCF channels, (ii) their density, number of layers and length, (iii) defect density in MWCNT (intrinsic and impurities), and (iv) doping of MWCNT are relevant to the application of MWCNT in PCF channels.

In this invention, results of selective growth of MWCNT in the PCF channels of a μGC preferably using selective Fe seeding and controlled growth technology are used.

The technology developed in this invention is also applied to design, fabrication and testing of a chemical nano-sensor chip. As the walls of MWCNTs can consist of 5 to 20 monolayers of $sp^2$-bonded carbon, they provide an ultra-large surface area for adsorption of different molecules that can be detected in the environment. This offers a possibility of chemical sensors with excellent sensitivity and fast response time. Initial experimental results of a nanosensor chip are also reported. The selectivity of MWCNT nanosensors is also of interest.

In one embodiment, multiwall carbon nanotubes (MWCNT), with a number of wall layers in a range from about 5 to about 30 and lengths up to 500 micrometers, are selectively grown inside the pre-concentrator focuser (PCF) section of an on-chip micro gas chromatograph (μGC) using a microwave plasma enhanced chemical vapor deposition method. The MWCNT growth, achieved using a Ti/Fe catalyst layer applied selectively inside the PCF channels, is disclosed. In addition to the high surface area, the desorption temperature of MWCNT is relatively low leading to a substantial reduction of energy consumption in PCF.

Multiwall carbon nanotubes, with wall layers in the range of 5-30 and lengths up to 500 micrometers are synthesized or fabricated by microwave plasma enhanced chemical vapor deposition using evaporated multi-layer Fe catalyst. The growth of MWCNT inside a deep reactive ion etched Si channel of the pre-concentrator focuser section of an on-chip micro gas chromatograph is provided by applying Fe (used as a catalyst) selectively in the channels. A MWCNT based chemical nanosensor has also been fabricated using the same technology and initial test results are reported.

EXAMPLE 1

Before the growth of high quality MWCNT inside the Si channels, MWCNT samples with different lengths were prepared on flat Si wafers to study the Fe (catalyst) application and patterning, the density and diameter of the tubes, and curling of the tube structure along the length. A double layer structure consisting of 10 nm titanium and 10 nm iron (the top layer) was deposited on p-type Si wafers to provide the Fe catalyst. The samples were treated in hydrogen plasma for 10 minutes using the microwave power of 1800 W and the hydrogen flow rate of 20 sccm with chamber pressure maintained at 40 torr. Then, methane was introduced into the chamber at a flow rate of 10 sccm keeping the other parameters the same. Keeping the sample temperature at 650° C., different tube synthesis times were studied as shown in FIG. 1, which indicates a growth rate was approximately 10 micrometer per minute.

Figure 2A:
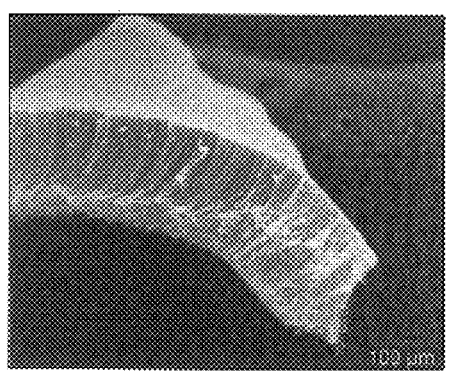
FIG. 2A is a SEM image of scraped MWCNT film grown for 15 minutes at 650° C.
Figure 2B:
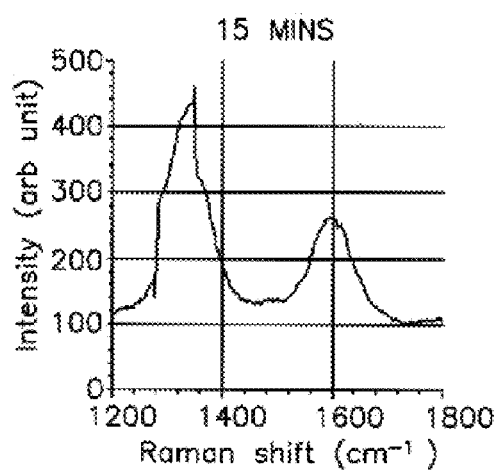
FIG. 2B is a graph showing Raman spectra.

SEM pictures of MWCNT samples grown for 15 minutes and 30 minutes are shown in FIG. 2A and FIG. 3A, respectively. The density of the tubes was approximately $4 \times 10^9$ tubes/cm$^2$. A Raman system (Raman System RSI-2001G) was also used to check the quality of the MWCNTs. FIGS. 2B and 3B show the Raman spectra of the 15 minutes sample and the 30 minutes sample. Both the FIGS. 3A and 3B show typical twin peaks at 1328-1340 cm$^{-1}$ (D-band) and 1576-1583 cm$^{-1}$ (G-band). The strong D-band indicates the common presence of defects. This result agrees with the TEM and SEM observations that the tubes were not straight but curly. A possible explanation on the presence of such defects is that during the high power plasma process, the ionized gas atoms will bombard the nanotube and introduce defects.

FIGS. 4A and 4B show the TEM pictures taken by using a JEOL 2010F field emission TEM. A 5-layer MWCNT and a 10-layer MWCNT were observed from the samples prepared above. For the 5 layer MWCNT, the inner diameter of the tube is 2.8 nm and the outer diameter is 7.2 nm. For the 10 layer MWCNT, the inner diameter is 3.2 nm and the outer diameter is 10.2 nm.

EXAMPLE 2

Figure 5A:
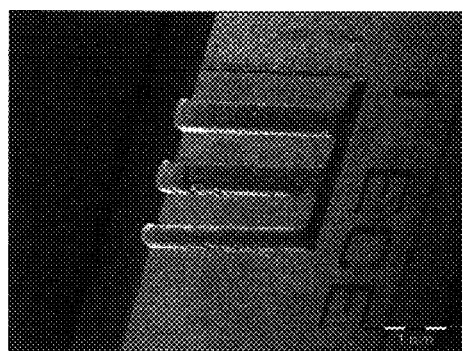
FIGS. 5A to 5D are SEM images of MWCNT growing inside the PCT channels.

The preconcentrator channels are fabricated in Si by deep reactive ion etched (DRIE) (FIG. 5A). There is photoresist on the bonding surface at the top of the channels. Then a titanium layer with a thickness of 10 nm and an iron layer with a thickness of 10 nm were separately deposited on the sample by e-beam evaporation at $5 \times 10^{-6}$ torr. The sample was dipped in methanol and ultrasonicated for 10 seconds to lift off the unwanted metal layers on the photoresist, which was left at the top of the channels after DRIE.

Then the sample was put in the MPCVD system, an Asmussen reactor. Prior to the growth of MWCNTs, the sample was treated by hydrogen plasma for 10 minutes with the microwave power at 1800 W and pressure at 40 torr. The flow rate for hydrogen is 20 sccm. Then methane was introduced in the system with flow rate of 10 sccm. The synthesis time is 15 minutes. Then the sample was cooled down to room temperature in vacuum. After the synthesis the sample was examined by the JEOL 6400V SEM. A 21 nm gold layer was sputtered prior to the examination.

EXAMPLE 3

Figure 5B:
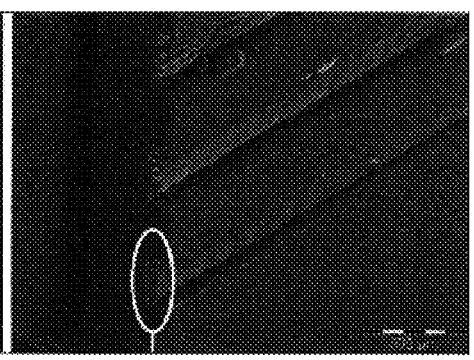
Figure 5C:
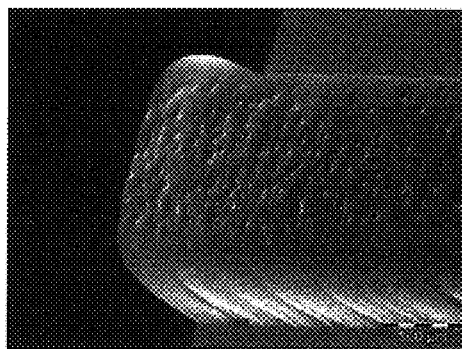
Figure 5D:
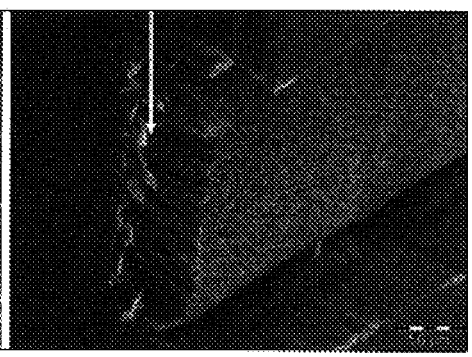

The growth conditions for MWCNT were similar to those described earlier except that the pressure was 40 torr. The growth temperature was carefully controlled at 650° C. because, in the case of growth inside the channels, the increase of temperature was observed. After a synthesis time of 15 minutes the sample was cooled down to room temperature in vacuum. A 21 nm gold layer was sputtered on the sample prior to the SEM examination. FIGS. 5B, 5C and 5D show the sample after the synthesis of MWCNTs. The length of the tube is about 50 micrometers; the density of the tube is about $4.2 \times 10^9$ tubes/cm$^2$. The tubes were only grown at the bottom of the Si channels, the top surface is clean and ready for bonding.

EXAMPLE 4

Figure 6A:
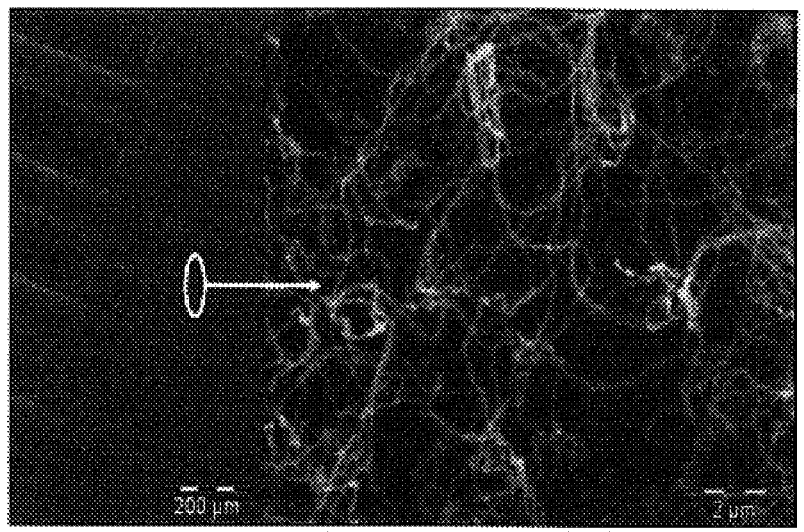
FIG. 6A is a SEM image of a first generation sensor test chip.
Figure 6B:
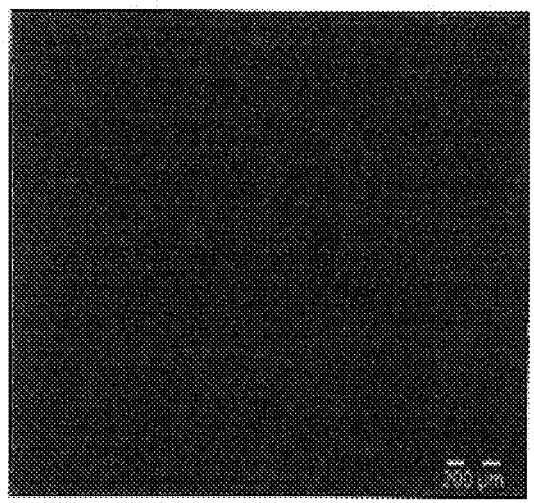
FIG. 6B is a closeup of the MWCNT.

A chemical nanosensor was also fabricated utilizing the disclosed method. The sensor structure was fabricated on a quartz substrate to eliminate the possible leakage current of from the silicon. A titanium layer with a thickness of 10 nm and an iron layer with a thickness of 10 nm were deposited on the sample by e-beam evaporation at $5 \times 10^{-6}$ torr. The metal layers were patterned to form the electrode. The gap between the electrodes was 200 micrometers. Then the sample was placed in the microwave plasma enhanced chemical vapor deposition (MPCVD) system to growing MWCNT. The growth condition is the same as the condition used to grow MWCNT in the preconcentration channels except that the synthesis time was 30 minutes. The length of the tube is about 400 micrometer. FIGS. 6A and 6B show the sensor structure.

Figure 7:
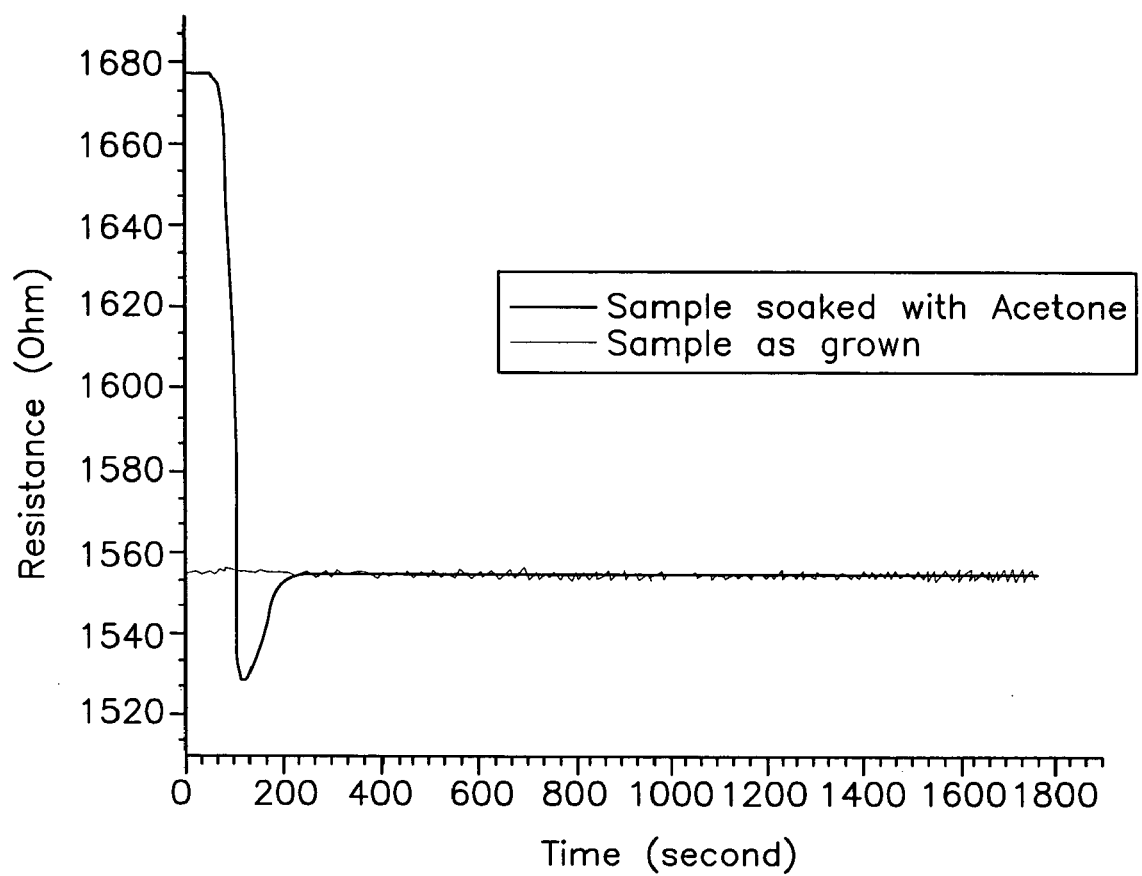
FIG. 7 is a graph showing resistance vs. time for the device of FIG. 6A.

The fabricated sensor was connected with a Keithley 2010 multimeter to monitor its resistance change. FIG. 7 shows the response of the sensor to the exposure of acetone. The readout showed that the resistance of the sensor structure changed 150 ohm during the experiment.

Generally speaking and with regard to an exemplary PCF device, MWCNT, with wall layers in the range of about 5 to about 30 and lengths up to about 500 micrometers selectively grown inside the pre-concentrator focuser section of an on-chip μGC, have ultra high surface area and low energy consumption in PCF. They have superior adsorption/desorption characteristics as compared to other known materials. Also MWCNT based sensor shows promising properties for sensing the organic compounds.

EXAMPLE 5

Figure 8A:
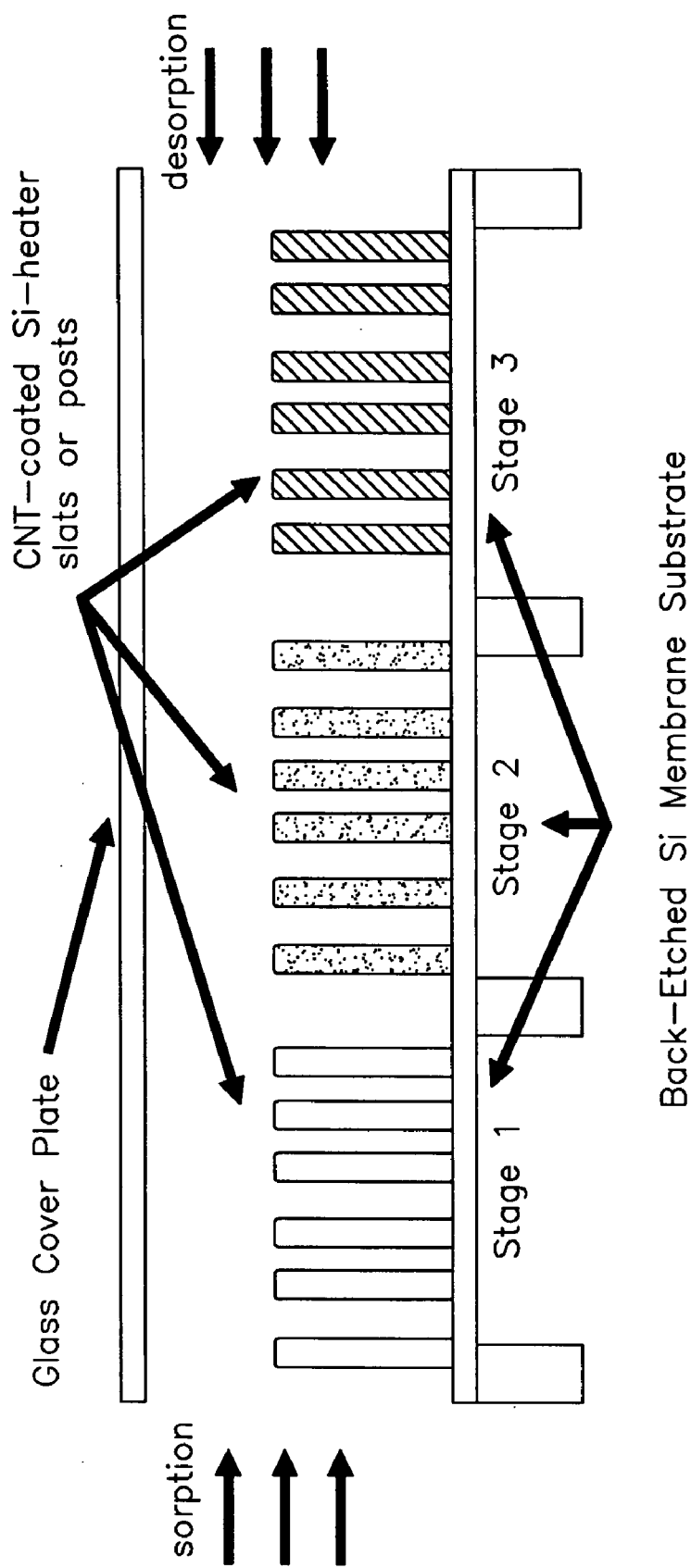
FIGS. 8A and 8F are diagrams of a microfabricated preconcentrator employing conformally-coated layers of carbon nanotubes on a high-aspect-ratio heater element.
Figure 8B:
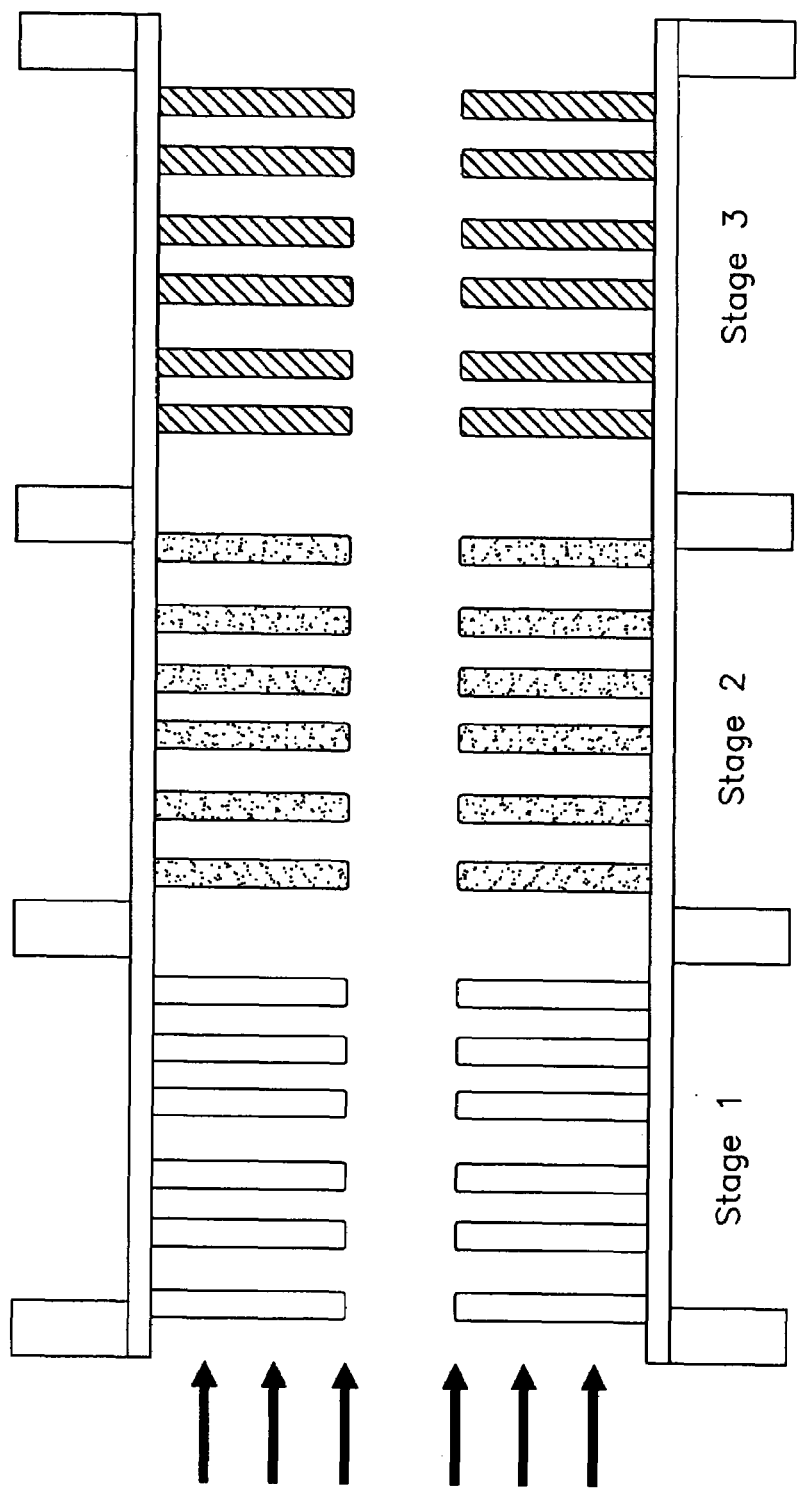
FIG. 8B is a sandwich structure.
Figure 8C:
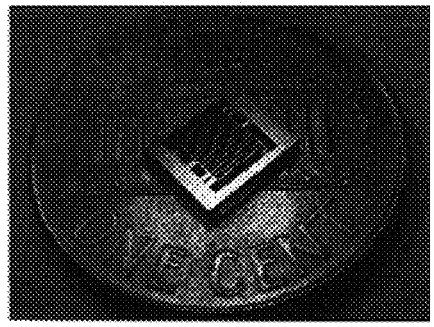
Figure 8D:
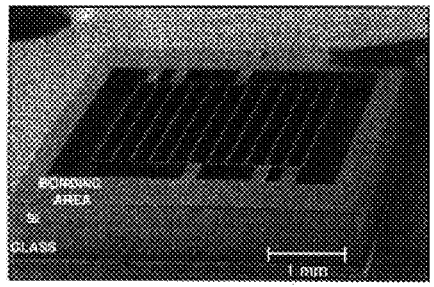
Figure 8E:
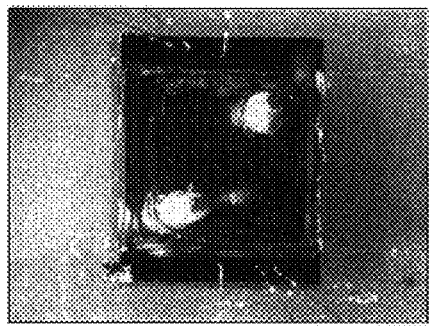
Figure 8F:
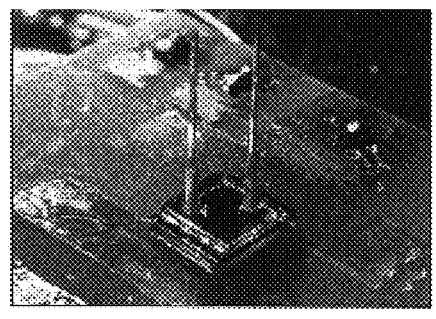

FIGS. 8A and 8B show two renditions of a microfabricated preconcentrator comprising a series of high-aspect-ratio Si posts or slats supported on a thin membrane of Si and capped with a glass cover plate having inlet and outlet ports at the glass-silicon juncture or elsewhere. Photographs in FIGS. 8C to 8F are prototype microfabricated Si preconcentrators with the planned heater structures (slats). The dimensions of the single-stage heater are roughly 3 mm (1)×3 mm (w)×0.5 mm (h). The CNTs are deposited onto the top and lateral surfaces of the slats or posts so that an incoming air stream containing organic vapors would flow over the CNT layers and are trapped. After collection of a certain volume of vapors, a current is applied through the Si heater structure to raise the temperature rapidly and the vapors are desorbed from the CNTs and swept under a flow of air to downstream components for separation and/or detection. After cooling to room temperature, this cycle starts again. The preconcentrator can consist of a single section or three contiguous sections where each section has a different type of CNT (different surface area, thickness, etc. that would alter its adsorptive properties).

Figure 9:
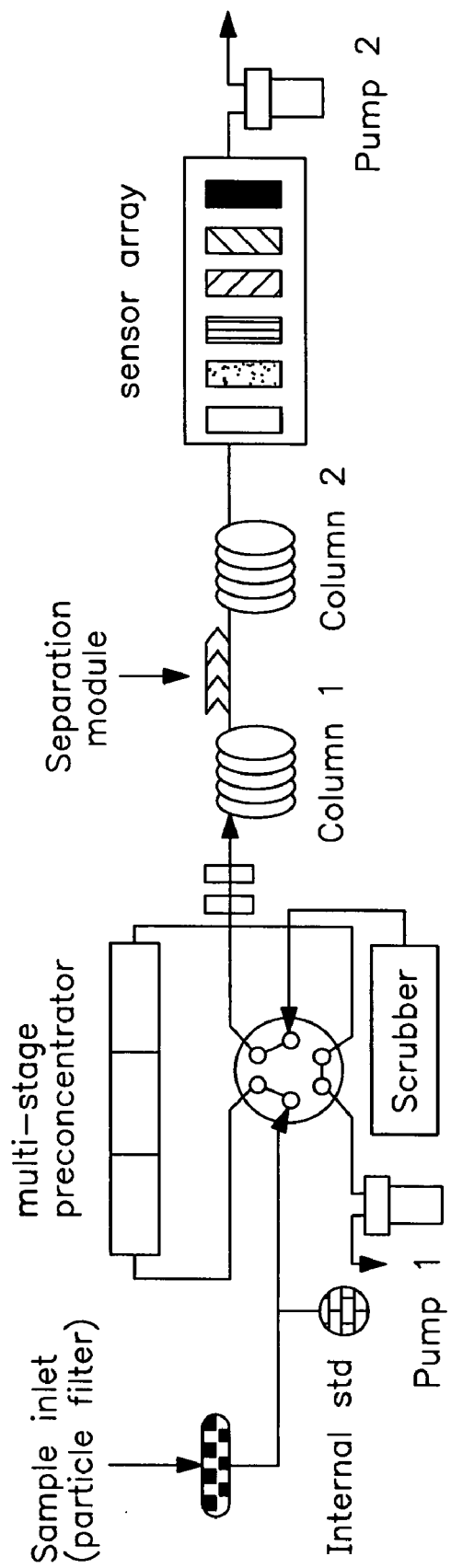
FIG. 9 is a schematic diagram of a microanalytical system in which the CNTs are used as part of the preconcentrator, separation module or sensor array.

FIG. 9 shows a diagram of a microanalytical system as a preconcentrator. Trapped vapors are desorbed from the preconcentrator and pass to a separation stage (Columns 1 and 2) and then onto a sensor array for detection. The system is made of miniaturized, interconnected (which can be integrated) subcomponents and occupy a total volume of several cubic cm.

EXAMPLE 6

FIGS. 5A to 5D show a series of photographs illustrating CNT layers that were produced on surfaces, including a slat-type surface similar to that used in the microfabricated heater structure of FIG. 8A, made of silicon with a thin metal coating.

EXAMPLE 7

Figure 10:
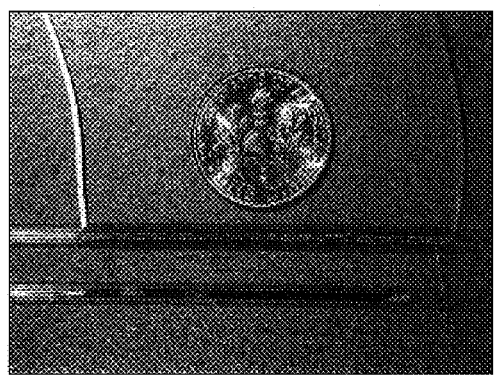
FIG. 10 is a photograph of a conventional preconcentrator consisting of a glass capillary (~1 mm i.d.) packed with granular adsorbent material. This configuration was used to test the CNTs to generate data presented in Table 1 which demonstrates the utility of this invention using a prior art method.
Figure 11:
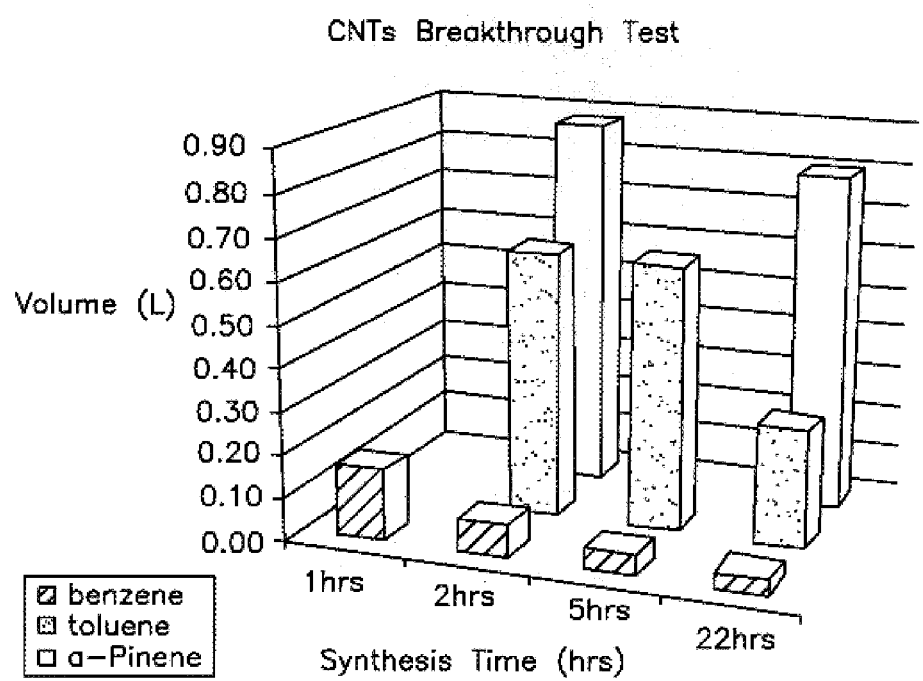
FIG. 11 is a graph showing test data showing the breakthrough volume (an indication of vapor capacity) of three test vapors (benzene, toluene, and alpha-pinene) as a function of synthesis time of the CNTs.

FIG. 10 shows a conventional preconcentrator tube packed with granular adsorbent material. This configuration was used for generating the test results shown in FIG. 11 and Table 1 with CNTs that were produced.

TABLE 1

Desorption efficiency test on a sample of CNTs packed into a glass capillary, loaded with each of several vapors individually and thermally desorbed under controlled conditions. Peak widths, which provide an indication of desorption efficiency, are given in the last column.

| | | Desorption Peak width Test | | | | |
|---|---|---|---|---|---|---|
| Trial No. | Chemicals | FW | Pv(torr) | C (ppm) | V(ml) | Peak Width (sec.) |
| 1 | Acetone | 58.1 | 231 | 100 | 0.25 | 0.9 |
| 2 | Benzene | 78.1 | 95 | 100 | 0.25 | 0.9 |
| 3 | Toluene | 92.1 | 28.5 | 100 | 0.25 | 1.3 |
| 4 | m-xylene | 106.2 | 8 | 100 | 0.25 | 1.5 |
| 5 | n-nonane | 128.26 | 4.3 | 100 | 0.25 | 1.6 |
| 6 | d-limonene | 136.24 | 3 | 100 | 1.00 | 2.0 |
| 7 | D5 | 370.77 | 1.5 | 100 | 0.25 | 3.1 |
| 8 | Butoxyethanol | 118.18 | 0.85 | 100 | 0.25 | 1.9 |
| 9 | Naphthalene | 128.17 | 0.08 | Sat. 105 | 0.25 | 3.8 |
| 10 | n-tridecane | 184.36 | 0.04 | Sat. 53 | 0.50 | 7.2 |

Conditions:
Sampling conditions: flow rate of 15.5 ml/min for 3 min (only 1 min for acetone) drawn from a test atmosphere containing the vapor at 100 parts-per billion v/v.
Desorption Temperature: 300° C.
Desorption Time: 1 min
Inlet Pressure: 2 PSI
Backflush flow rate: 2.17 ml/min
Capillary preconcentrator packed with 2.46 mg of CNTs (synthetic condition: growth time = 2 hrs)
Pv = vapor pressure in Torr
FW = molecular FIG. 11 and Table 1 show data from preliminary testing of the adsorption capacity and thermal desorption efficiency, respectively, of samples of CNTs produced by and tested with several vapors. In this case, the CNTs were deposited onto a separate substrate and then scraped off and packed into a small glass capillary wrapped with a Pt-wire coil for heating (see FIG. 10). Results are encouraging and show behavior of the carbon nanotubes formed by CVD that is comparable to, or superior to, common commercial granular adsorbent materials tested in a similar fashion.

The CNTs used in these tests were produced using a known microwave plasma chemical vapor deposition (MPCVD) process whereby a substrate, in this case a silicon wafer, is first coated with a catalytic metal layer, in this case Fe or Ni, and then placed in a chamber. A microwave plasma is generated and the chamber is heated to a temperature in the range of 450-850° C. Feed gases ($N_2/H_2/CH_4$) (percentages) are introduced into the heated chamber and a reaction takes place at the surface to yield CNTs which continue to grow up from the surface at a rate that depends on the metal, reaction conditions, and time.

EXAMPLE 8

Figure 12A:
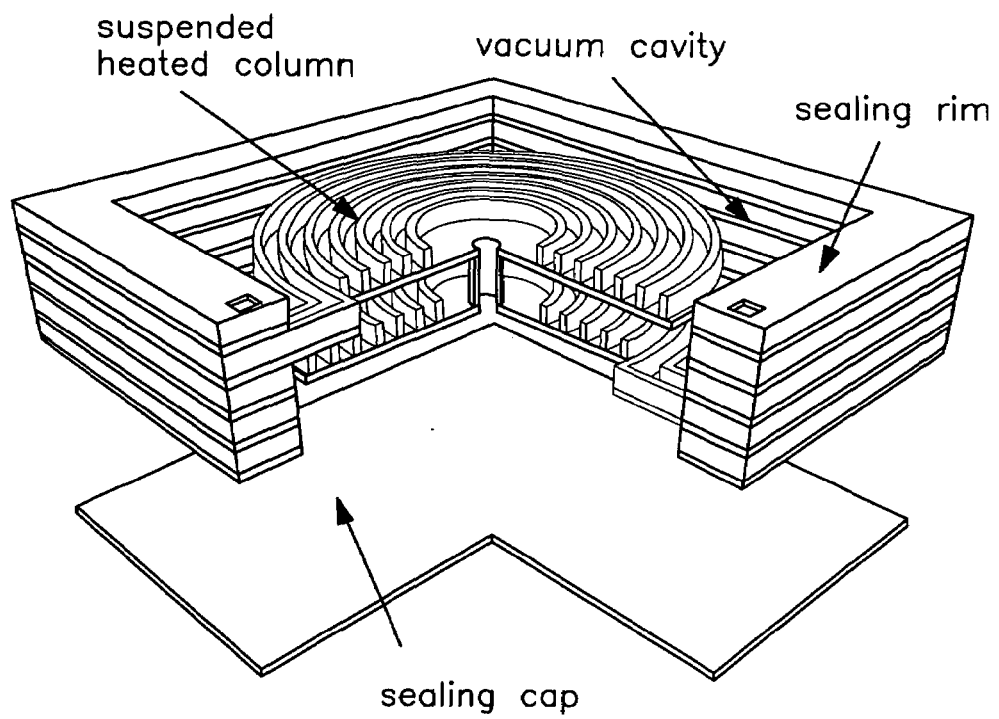
FIGS. 12A to 12E are etched-Si channels to be used for the microfabrication of a chromatographic separation column in a microanalytical system.
Figure 12B:
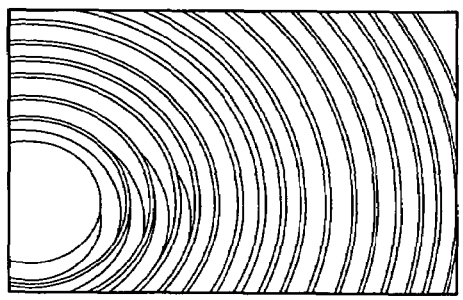
Figure 12C:
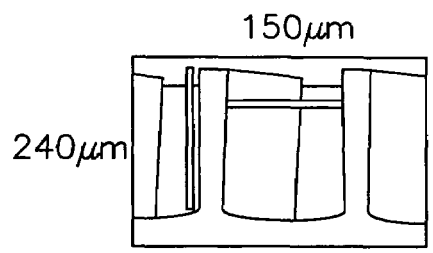
Figure 12D:
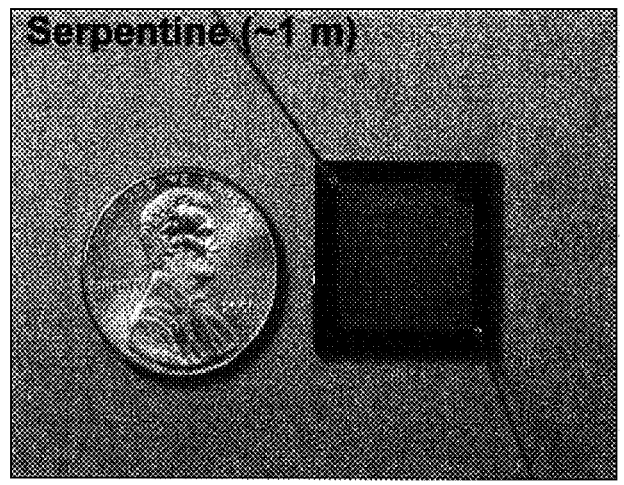
Figure 12E:
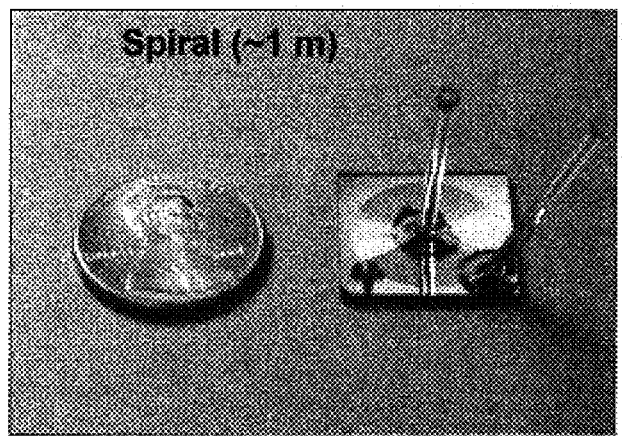

FIGS. 12A to 12E show a diagram and photographs of etched-Si channels to be used for the microfabrication of a chromatographic separation column in a microanalytical system. FIG. 12A presents a conceptual diagram of stacked, interconnected series of channel chips; FIG. 12B shows a scanning electron micrograph of a spiral-etched column chip (inset FIG. 12C) shows dimensions of the channel cross section; and FIG. 12D is a photograph of individual channel chips with spiral and serpentine etched channels and a total length of just less than 1 meter. The CNTs are conformally deposited within these channels and serve as the stationary phase for effecting separations (after capping and interconnecting the separation module to other system components).

FIG. 13A shows a drawing of an array of sensors, each coated with a differing CNT, leading to a characteristic response pattern for a hypothetical vapor, arising from differential (and reversible) adsorption onto the different CNTs on the sensors as shown in FIG. 13B that can be used for vapor recognition ('finger printing').

EXAMPLE 9

Multiwall carbon nanotubes, with wall layers in range of 5-30 and lengths of up to 500 micrometers, were synthesized by microwave plasma enhanced chemical vapor deposition using evaporated multi-layer Fe catalyst. The growth of nanotubes with a density of $5\times10^9$ cm$^{-2}$ inside 100 micrometer deep Si channels of the pre-concentrator focuser (PCF) section of an on-chip micro gas chromatograph (µGC) was accomplished by applying the catalyst selectively in the channels. The technology developed for PCF was used to fabricate MWCNT-based chemical nanosensors.

The nanostructures present in multiwall carbon nanotubes (MWCNT) provide a very large surface area as compared to conventional materials. As the number of layers in a MWCNT, and therefore diameter of the MWCNT, can be changed through growth conditions, the storage or adsorption sites for different gas molecules can be adjusted in a unique way. Experimental results show that the desorption temperature of MWCNT is approximately 200° C., as compared to 300° C. for a typical adsorption material, which dramatically reduces the energy consumption in the preconcentrator focuser (PCF) stage of a micro gas chromatograph (µGC) making MWCNT an ideal material for on-chip µGC (Zellers, E. T., et al., in: Proc. Symposium on Materials, Mechanisms, and Systems for Chemical and Biological Detection and Remediation, Materials Research Society Meeting. San Francisco, Calif., (April 2004); Aslam, D. M., et al., in: Proc. SENSOR EXPO, Detroit, Mich., (June 2004); Tian, W. C., et al., J. MEMS 12 264-272 (2003): and Aslam, D. M., et al., in: Proc. COMS, Ypsilanti, MI (2002)). However, the reproducibility of high-quality MWCNTs selectively grown in PCF channels, the density of MWCNT, number of layers and length of MWCNT, defect density in MWCNT, and doping of MWCNT are very important issues related to the application of MWCNT in PCF channels. In this Example, results of selective growth of MWCNT in the PCF channels of a µGC using selective Fe seeding and controlled growth technology are described.

The technology developed in this invention is also applied to design, fabrication and testing of a chemical nano-sensor chip. As the walls of MWCNTs can consist of 5 to 30 monolayers of sp$^2$-bonded carbon layers, they provide an ultra-large surface area for adsorption of different molecules found in the environment. This provides chemical sensors with excellent sensitivity and fast response time.

Figure 14A:
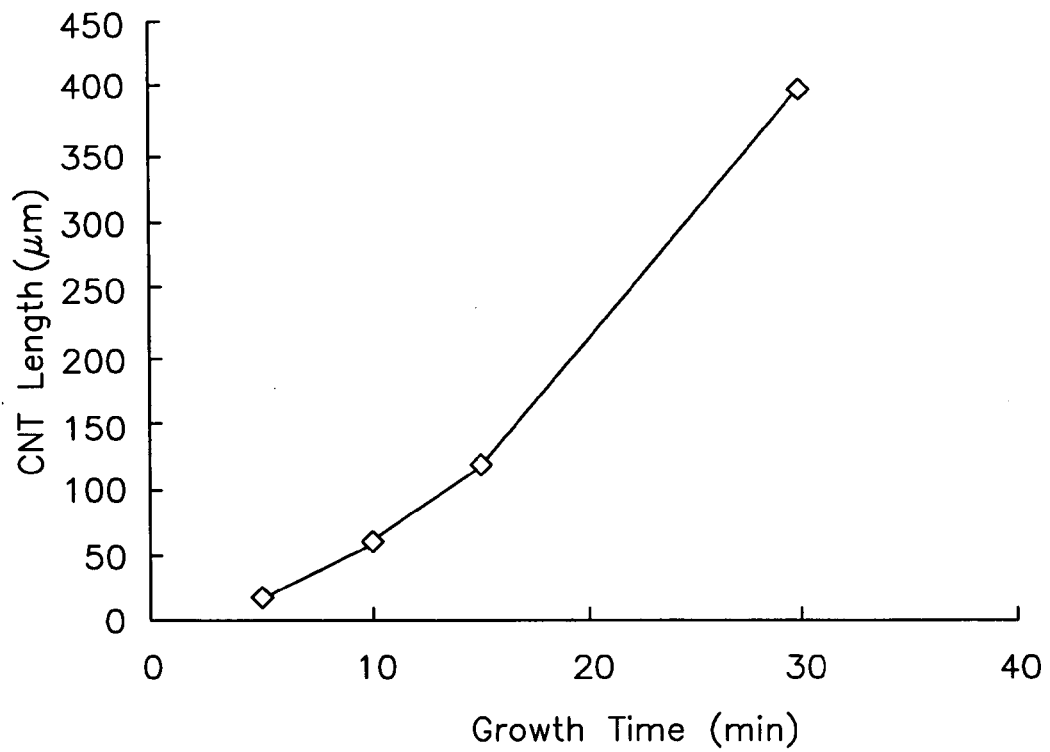
FIG. 14A is a graph showing MWCNT length as a function of synthesis time.

Before the growth of high quality MWCNT inside the Si channels, MWCNT samples with different lengths and diameters were prepared on flat Si wafers to study the density, catalyst application and diameter of the tubes. A double layer structure consisting of 10 nm titanium and 10 nm iron was fabricated on p-type Si wafers to provide the Fe catalyst. The samples were treated in hydrogen plasma for 10 minutes before increasing the microwave power to 1600 W. The hydrogen gas flow rate was 20 sccm and the pressure was kept at 40 torr. After the hydrogen plasma treatment, methane was introduced into the system at a flow rate of 10 sccm. The MWCNT were grown at 650° C. using different synthesis times in a microwave plasma chemical vapor deposition (MPCVD) system. As shown in FIG. 14A, the growth rate is approximately 10 micro-meters per minute (Kim, U., et al., J. Vac. Sci. technol. B21 1291-1296 (2003)). The density of the tubes was approximately $4\times10^{19}$ cm$^{-2}$.

Figure 14C:
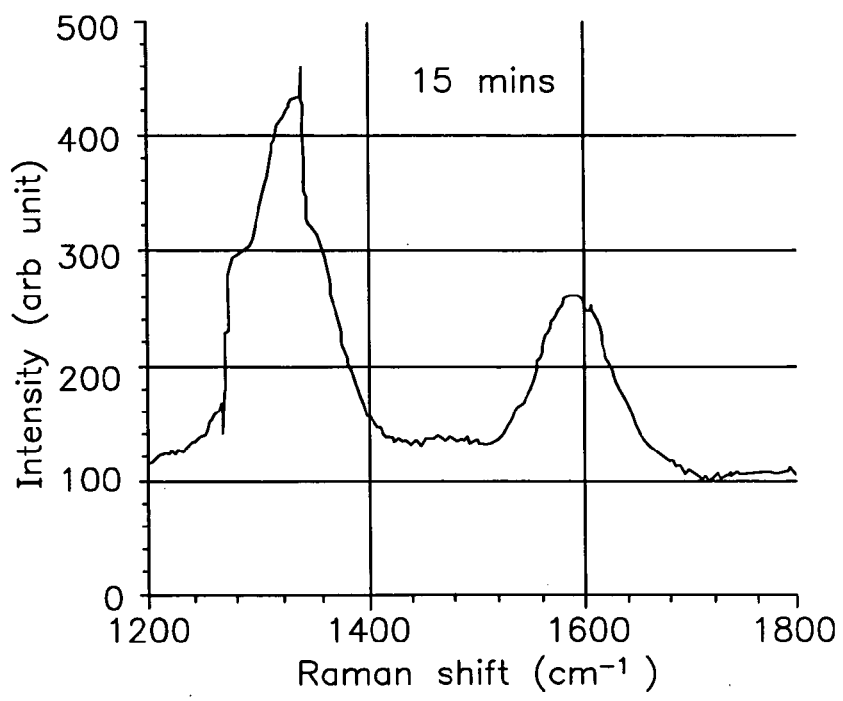
FIG. 14C is a Raman of the 15 min. sample.
Figure 14B:
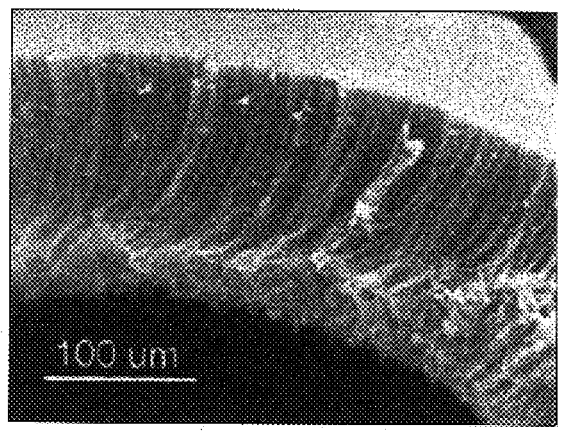
FIG. 14B shows SEM of MWCNT with 15 min. synthesis time.
Figure 14D:
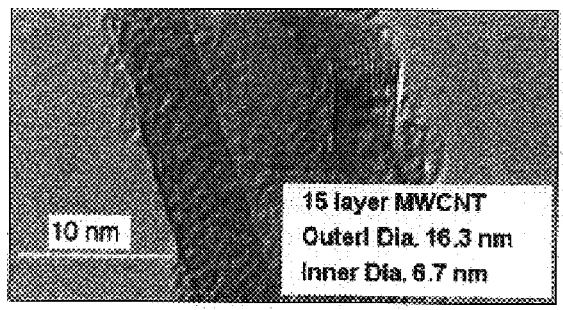
FIGS. 14D and 14E show TEM of the MWCNT showing different diameters.
Figure 14E:
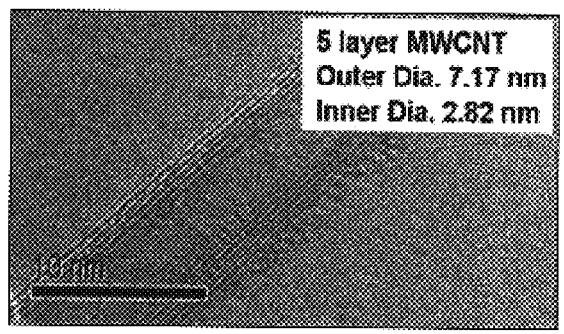

SEM pictures of MWCNT samples grown for 15 minutes are shown in FIG. 14B. Raman spectroscopy, used to check the quality of the nanotubes, as depicted in FIG. 14C, reveals typical twin peaks at 1328-1340 cm$^{-1}$ (D-band) and 1576-1583 cm$^{-1}$ (G-band). The strong D-band indicates the presence of defects, which seem to have resulted from curling of the tubes as seen in the transmission electron microacope (TEM) pictures depicted in FIG. 14D. FIG. 14E shows a TEM of tubes prepared using a different catalyst application method in an earlier study (Kim, U., et al., J. Vac. Sci. Technol. B21 1291-1296 (2003); and Kim, U., et al., Diamond relat. Mater. 10 1947-1951 (2001)). The TEM images seem to indicate that the D-band in Raman spectra may not be due to amorphous carbon in the tubes.

Figure 15A:
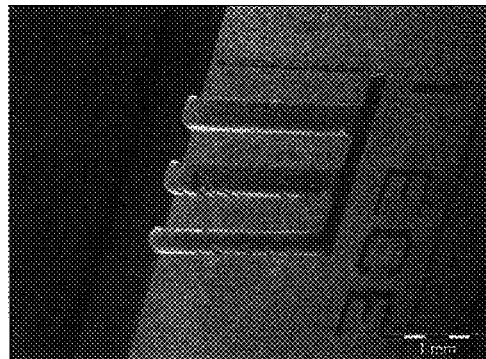
FIGS. 15A to 15D are SEM of MWCNT growing inside the PCF channels.
Figure 15C:
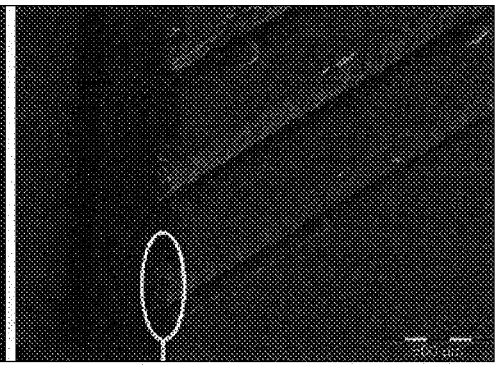
Figure 15B:
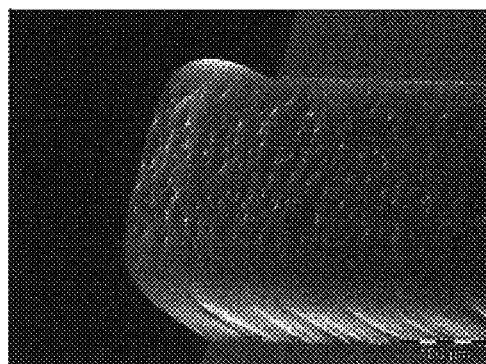
Figure 15D:
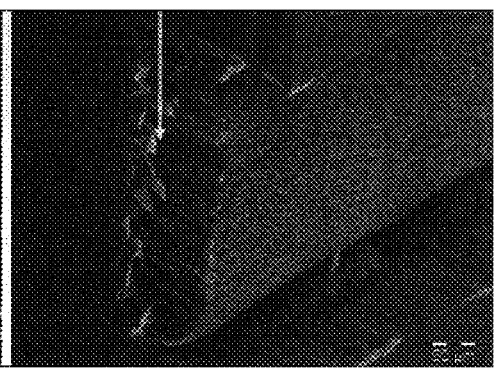

The PCF channels are fabricated in Si by deep reactive ion etching (DRIE) as shown in FIG. 2A. Then, a Fe/Ti double layer structure was deposited on the sample by e-beam evaporation at $5\times10^{-6}$ torr. The sample was coated with photo resist and a mask was used to do the lithography. After the photo resist was developed, as shown in FIG. 15B, the metals on the top surface of PCF were etched in diluted HF (2%). The growth conditions for MWCNT were similar to those described earlier except that the pressure was 40 torr. The growth temperature was carefully controlled at 650° C. because, in the case of growth inside the channels, the increase of temperature on the sample surface was observed. After a synthesis time of 15 minutes the sample was cooled down to room temperature in vacuum. FIGS. 15C and 15D show the sample after the synthesis of MWCNTs. The length of the tubes is approximately 50 micrometers and the density of the tubes is $4.2\times10^9$ cm$^{-2}$. The tubes were only grown inside the Si channels leaving the top surface clean and ready for bonding.

EXAMPLE 10

Recent studies on the use single-wall CNTs as a chemical sensors (Valentini, L., et al., Appl. Phys. Lett. 82 961-963 (2003); and Kong, Jing, et al., Science 287 622-625 (2000)) show that the resistance of CNTs changes when exposed to chemicals. The use of MWCNTs as chemical sensors is described. A nanosensor testchip was designed and fabricated on a quartz substrate to eliminate the possible leakage current from the substrate. A Fe/Ti double layer, deposited using a procedure described above in Example 3, was patterned to form the electrodes consisting of a finger structure with a gap of 200 micrometers. After the growth of MWCNT with a length of 400 micrometers on the electrodes, it was found that the tubes from the neighboring electrodes overlapped forming a resistive sensor structure. FIGS. 6A and 6B shows the sensor details and the overlapping of tubes.

Figure 16A:
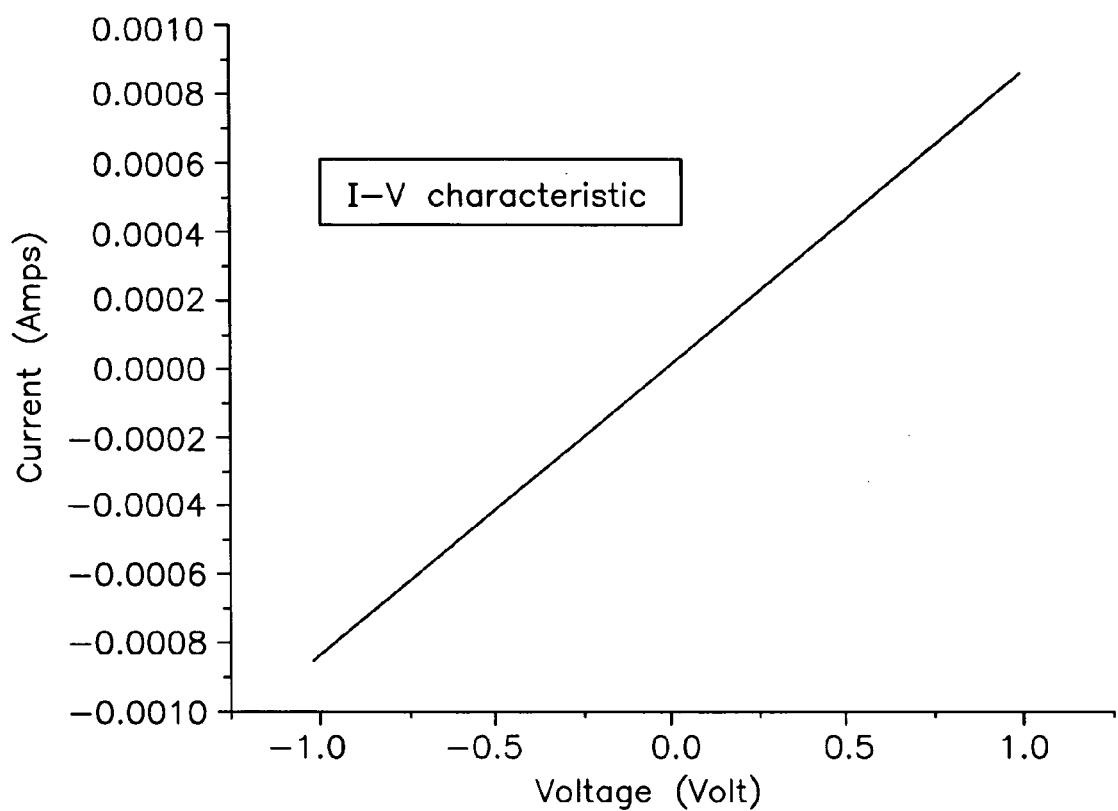
FIG. 16A is a resistance measurement of the sensor structure in air.
Figure 16B:
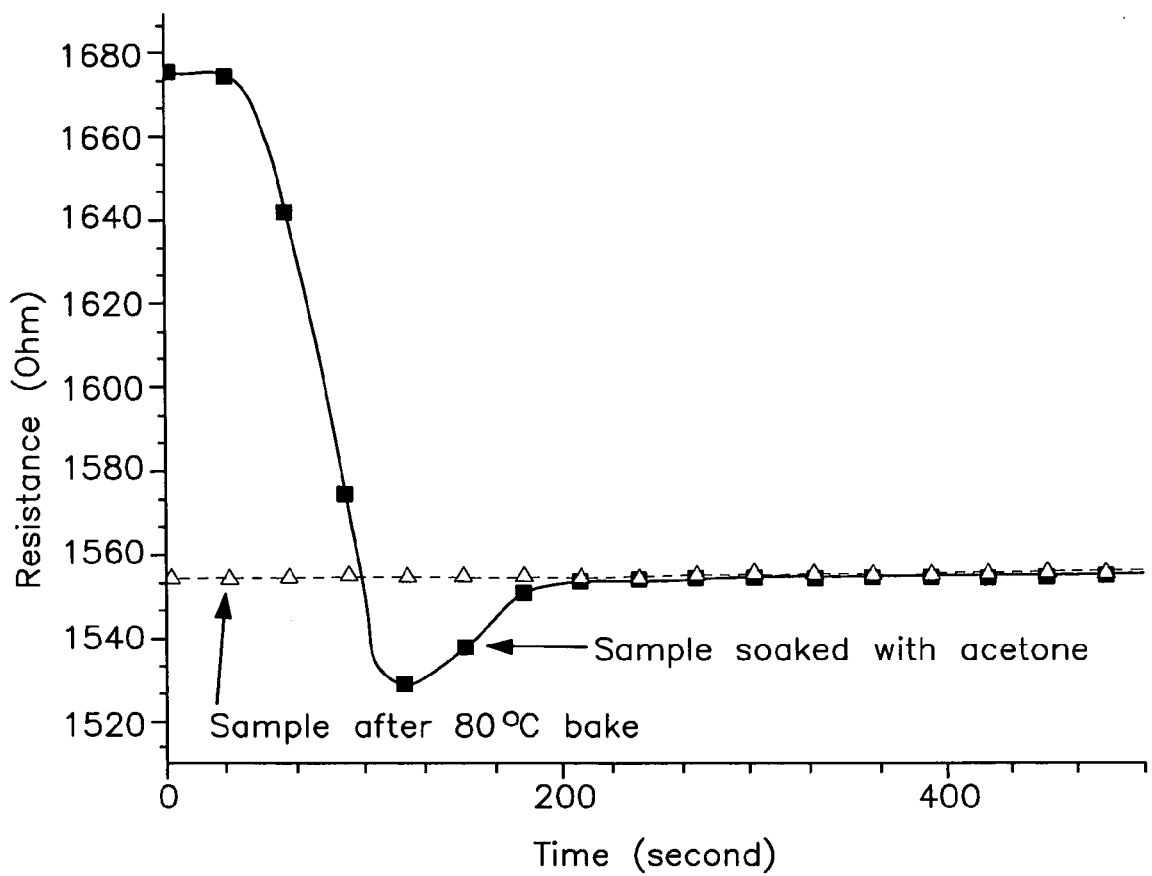
FIG. 16B is a graph of an I-V characteristic of the sensor structure in vacuum at 25° C.

The fabricated sensor was placed inside a high vacuum chamber on a temperature stage. The pressure inside the chamber was kept at $2\times10^{-7}$ torr. The surface temperature of the sensor structure was measured by a K type thermal couple. The measured current-voltage (I-V) characteristics of the sensor structure, as shown in FIG. 16B, reveal that the sensor behavior is ohmic. The sensor resistance, measured for a large number of samples in vacuum at 300 K, was found to be in the range of 1,200-1,400 ohms.

When the samples were exposed to air at the ambient pressure, the change in sensor resistance was 0.1% for all samples tested. However, when the sensor was soaked in acetone at ambient pressure, there was rapid increase in sensor resistance (approximately 8%) as shown in FIG. 16A. When the acetone evaporated, the resistance decreased before stabilizing to its original resistance.

Figure 17:
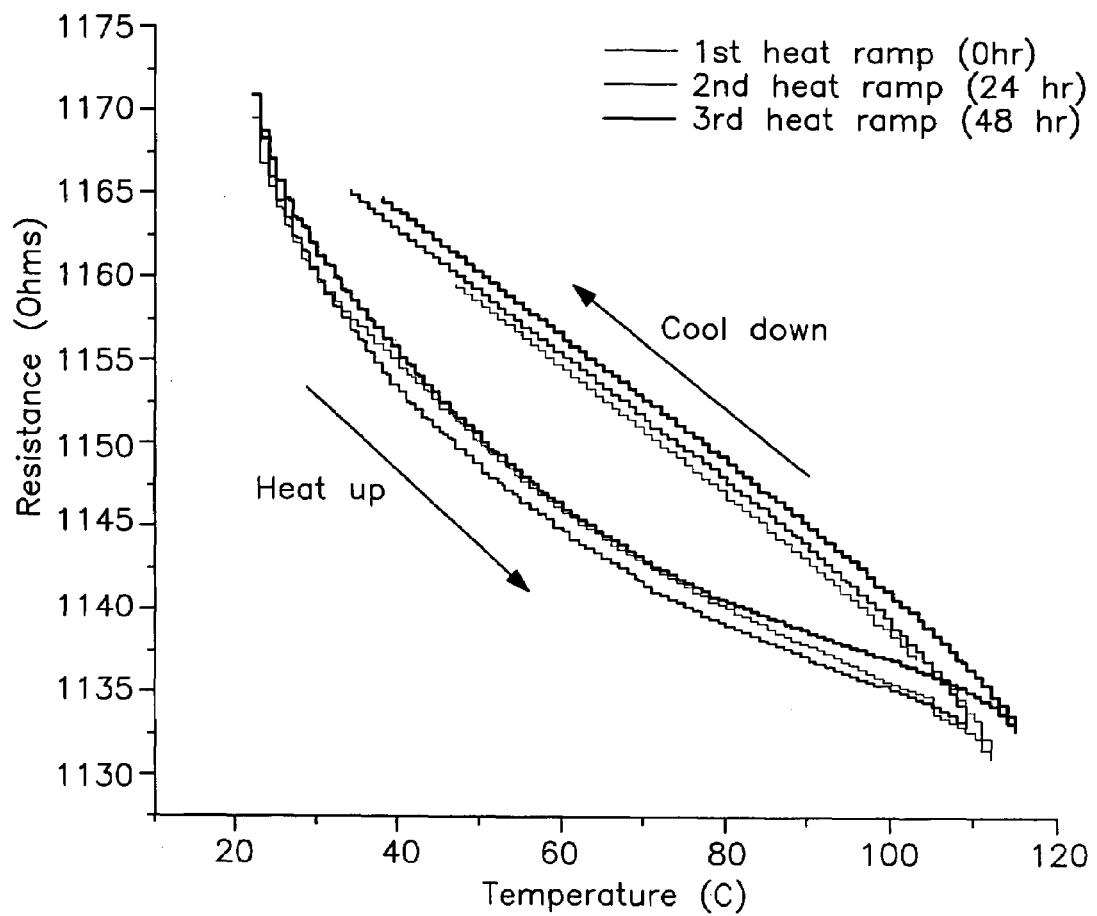
FIG. 17 is a graph of resistance-temperature response of the sensor structure in vacuum.

FIG. 17 shows the resistance-temperature response of the sensor structure in vacuum. When the sample was heated up, the pressure inside the vacuum chamber increased from $2 \times 10^{-7}$ torr to $1 \times 10^{-6}$ torr. A resistance hysteresis was also observed during the temperature cycle. This phenomenon appeared even after 48 hours inside the vacuum chamber and two temperature cycles.

MWCNTs, with wall layers in range of 5-30 and lengths up to 500 micrometers selectively grown inside the pre-concentrator focuser section of an on-chip μGC, have ultra high surface area and low energy consumption in PCF. They have superior adsorption/desorption characteristics as compared to other known materials. Also MWCNT based sensor shows promising properties for sensing the chemicals.

In summary, a device for collecting or concentrating gaseous, vaporous or other matter is disclosed. The device includes a heater structure and a carbon nanotube coating positioned on the heater structure. The carbon nanotube coating is capable of adsorbing the gaseous, vaporous, or other matter when the carbon nanotube coating is at a first temperature and wherein the carbon nanotube coating is capable of desorbing the gaseous, vaporous, and other matter when the heater structure heats the carbon nanotube coating to a second temperature.

The heater structure may define a set of channels, and each channel may have high-aspect ratio walls. The carbon nanotube coating can be a region or layer selectively disposed on the walls such that only one or more portions of the walls are covered by the carbon nanotube coating. The portions include a bottom section of the walls of each channel such that a top surface of the heater structure is not covered by the carbon nanotube coating. The top surface is a bonding surface.

The carbon nanotube coating can include a multiwalled carbon nanotube structure. The multiwalled carbon nanotube structure may include a range of monolayers of carbon where the range is from about 5 to about 30. The heater structure can also include a catalyst layer disposed on the portions of the walls to be covered by the multiwalled carbon nanotube structure. The catalyst layer can include an iron layer, and can further include a titanium layer disposed between the iron layer and the heater structure.

The device can be used as a concentrator and/or focuser in combination with a micro-gas chromatograph.

A method of making a pre-concentrator for a gas or vapor is also disclosed. The method includes the steps of fabricating channels by etching a semiconductor substrate, applying a catalyst to a portion of each channel, and growing a carbon nanotube structure on the portion of each channel having the applied catalyst.

The portion of each channel to which the catalyst is applied can include a bottom portion, such that a top portion of the vapor pre-concentrator is not covered by the carbon nanotube structure. The method can further include the step of bonding the vapor pre-concentrator to a separate structure to further define the channels. The separate structure can include a further semiconductor substrate associated with a further vapor pre-concentrator.

The catalyst can include an iron layer and may further include a titanium layer disposed between the iron layer and a surface of the semiconductor substrate. The applying step can include the step of depositing the titanium and iron layers via e-beam evaporation.

The channel fabricating step can include the step of deep reactive ion etching (DRIE) the semiconductor substrate or any other etching method or any other method of making channel.

The step of growing the carbon nanotube structure can include a microwave plasma chemical vapor deposition step.

A method of collecting a vapor, gas or other matter is also disclosed. The method includes the steps of exposing a carbon nanotube preconcentrator to the vapor, gas or other matter to allow a carbon nanotube structure of the carbon nanotube preconcentrator to adsorb the vapor, gas or other matter, and heating the carbon nanotube structure to desorb the vapor, gas or other matter.

The heating step can include the steps of heating the carbon nanotube structure to a number of temperatures to desorb selectively a number of vapors, gases or other maters in addition to the first-named vapor, gas or other matter.

As set forth above, multiwall carbon nanotubes (MWCNT), typically with diameters in the range of 7 to 20 nm and lengths in the range of 50-500 micrometers, have usually very high aspect ratios making them excellent nanostructures for use in the preconcentrator focusers (PCF) section of an on-chip micro gas chromatograph (μGC). As the walls of MWCNTs can consist of 5 to 20 monolayers of $sp^2$-bonded carbon layers, they provide an ultra-large surface area for adsorption of different vapors if the MWCNTs can be selectively grown in the PCF channels. In the disclosed development applying MWCNTs in AGC, high quality of MWCNTs inside deep reactive ion etched (DRIE) Si channels are grown while providing a clean bonding surface outside the channel.

The efficacy of adsorption/desorption characteristics of MWCNT has been shown, and MWCNTs were selectively grown in the PCF channels of a μGC. Experimental results show that, in addition to the high surface area, the desorption temperature of MWCNT is relatively low, which dramatically reduces the energy consumption in the PCF section of the μGC. The results, obtained by using selective seeding and controlled microwave plasma chemical vapor deposition (MPCVD) technology, is disclosed.

It is intended that the foregoing description be only illustrative of the present invention and that the present invention be limited only by the hereinafter appended claims.

We claim:

1. A method for the accumulation of an analyte as a vapor or gas and detection by a detection means which comprises:
    (a) providing a preconcentrator device with a heater structure which comprises (a) a non-conductive substrate in a container means having an opening for inlet of the analyte and an outlet for the analyte; a conductive strip bound to the substrate; a strip of a metal catalyst, which allows growth of nanotubes, mounted on the conductive strip; and (d) a lawn of carbon nanotubes which have been grown by chemical vapor deposition on the strip of the metal catalyst, wherein the nanotubes are adapted to accumulate the analyte inside the container means;

(b) introducing the analyte into the container means through the inlet means so as to accumulate the analyte in the carbon nanotubes;

(c) heating the nanotubes in the preconcentrator device with the heater structure to remove the analyte from the nanotubes in the container means through the outlet; and (d) detecting the gas analyte with the detection means.

2. The method of claim 1 wherein the detecting is with a gas chromatograph.

3. The method of claim 1 wherein the detecting means is a gas sensor means.

4. The method of claim 1 wherein the strip of the catalyst is a transition metal, the conductive strip is a metal, a conductor or semiconductor, and the substrate is a semiconductor or insulator.

5. The method of claim 1 wherein the substrate is a plate with a series of channels with the carbon nanotubes in the channels.

6. The method of any one of claims 1, 2, 3, 4 or 5 wherein the device is a MEMS device, wherein a surface area of the conductive strip is in the range of about 50 millimeters$^2$ or less.

* * * * *

UNITED STATES PATENT AND TRADEMARK OFFICE
CERTIFICATE OF CORRECTION

PATENT NO. : 7,615,189 B2  Page 1 of 1
APPLICATION NO. : 11/145292
DATED : November 10, 2009
INVENTOR(S) : Aslam et al.

It is certified that error appears in the above-identified patent and that said Letters Patent is hereby corrected as shown below:

Column 5, line 7, "log" should be --10g--.

Column 10, line 11, "$4 \times 10^{19}$" should be --$4 \times 10^9$--.

Column 12, line 37, "AGC" should be --µGC--.

Signed and Sealed this

Sixteenth Day of March, 2010

David J. Kappos
*Director of the United States Patent and Trademark Office*